(12) United States Patent
Deshpande et al.

(10) Patent No.: US 8,772,292 B2
(45) Date of Patent: Jul. 8, 2014

(54) PROCESS FOR THE PREPARATION OF A MEDICAMENT COMPRISING VARDENAFIL HYDROCHLORIDE TRIHYDRATE

(75) Inventors: Yogesh S. Deshpande, Aurangabad (IN); Sandra Brueck, Ottenhofen (DE); Julia Schulze Nahrup, Neuried (DE); Birgit Schnitter, Ulm (DE); Ganesh Gat, Pune (IN); Javed Hussain, Maharashfra (IN)

(73) Assignee: Ratiopharm GmbH, Ulm (DE)

( * ) Notice: Subject to any disclaimer, the term of this patent is extended or adjusted under 35 U.S.C. 154(b) by 620 days.

(21) Appl. No.: 12/600,446

(22) PCT Filed: Jun. 12, 2008

(86) PCT No.: PCT/EP2008/004755
§ 371 (c)(1),
(2), (4) Date: Jan. 29, 2010

(87) PCT Pub. No.: WO2008/151811
PCT Pub. Date: Dec. 18, 2008

(65) Prior Publication Data
US 2010/0159003 A1 Jun. 24, 2010

(30) Foreign Application Priority Data
Jun. 12, 2007 (DE) .......................... 10 2007 027 067

(51) Int. Cl.
*A61K 31/53* (2006.01)
*A61K 9/28* (2006.01)

(52) U.S. Cl.
USPC ........... 514/243; 424/474; 424/480; 424/465; 424/482

(58) Field of Classification Search
None
See application file for complete search history.

(56) References Cited

U.S. PATENT DOCUMENTS

2003/0211151 A1* 11/2003 Tillyer et al. ................. 424/468
2006/0111354 A1* 5/2006 Serno et al. .................. 514/243
2007/0071813 A1* 3/2007 Ahmed et al. ............... 424/464

FOREIGN PATENT DOCUMENTS

| DE | 10 2005 009 240 | 9/2006 |
| WO | WO-99/24433 A1 | 5/1999 |
| WO | WO-01/19357 A2 | 3/2001 |
| WO | WO 2004/006894 | 1/2004 |
| WO | WO 2005/110419 | 11/2005 |
| WO | WO 2005/110420 | 11/2005 |
| WO | WO 2006/092207 | 9/2006 |
| WO | WO 2006/092222 | 9/2006 |

OTHER PUBLICATIONS

Pharmaceutical Technology, Tableting & Granulation, The Granulation Process 101, pp. 8-13, 2002.*
Handbook of Environmental Data on Organic Chemicals, John Wiley & Sons, 4th Edition, 2001.*
Handbook of Pharmaceutical Additives, Synapse Information Resources Ince., 3rd Edition, p. 1473 and 1692, 2007.*
Handbook of Fillers, ChemTec Publishing, 2nd Edition, p. 154-163, 2000.*
"Sattigung (Physik)," Wikipedia, der freien Enzyklopädie. http://de.wikipedia.org/w/index.php?title=S%C3%A4ttigung_%28Physik%29&printable=yes. Accessed Jun. 20, 2008.
European Medicines Agency: European Public Assessment Report—Levtira—Scientific Discussion. http://www.ema.europa.eu/humandocs/PDFs/EPAR/Ievitra/621002en6.pdf. (2005).

* cited by examiner

*Primary Examiner* — David J Blanchard
*Assistant Examiner* — John P Nguyen
(74) *Attorney, Agent, or Firm* — Clark & Elbing LLP

(57) ABSTRACT

The present invention relates to a process for the preparation of a medicament containing vardenafil hydrochloride trihydrate in solid form, in which vardenafil hydrochloride trihydrate is processed with suitable pharmaceutical auxiliaries at a temperature of from approx. 20° C. to approx. 45° C.

21 Claims, 3 Drawing Sheets

Rel. weight

Figure 1:
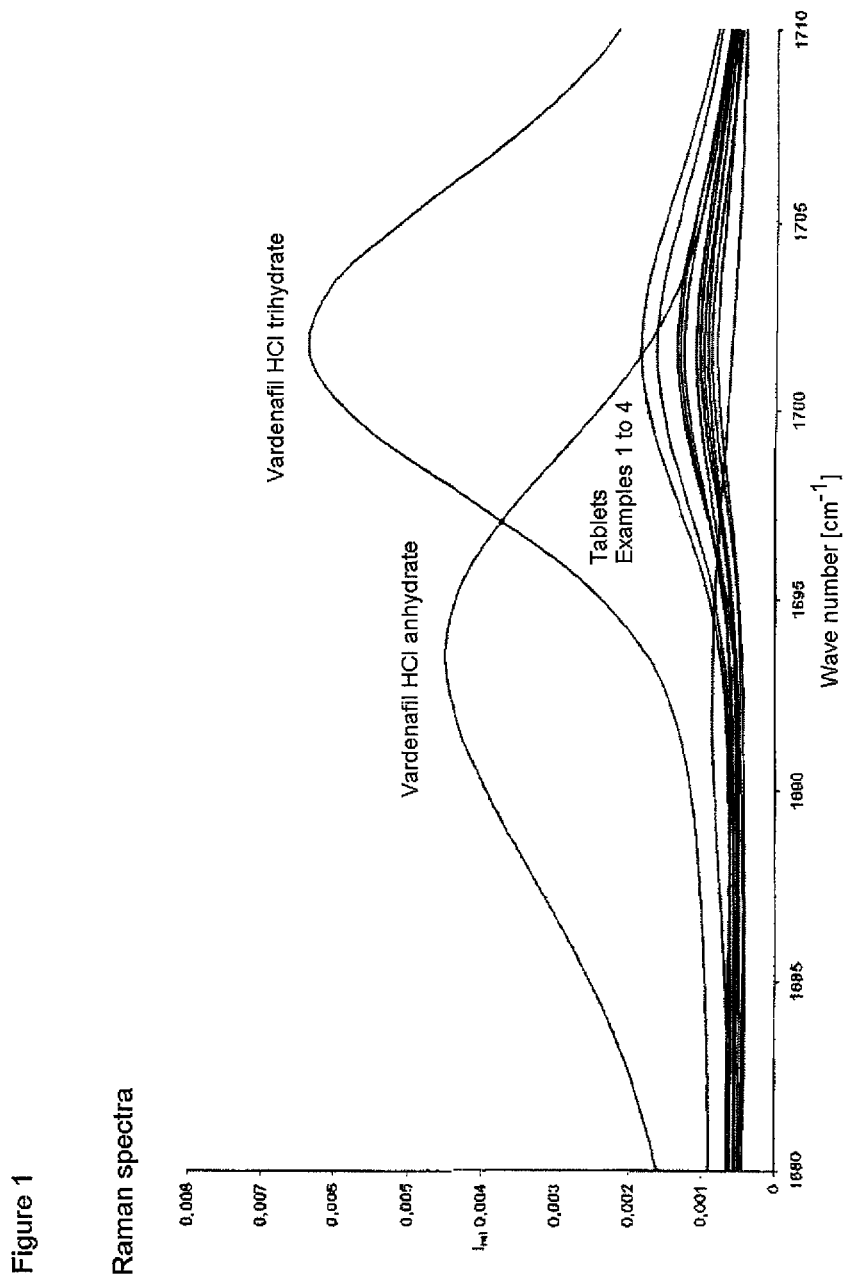

PROCESS FOR THE PREPARATION OF A MEDICAMENT COMPRISING VARDENAFIL HYDROCHLORIDE TRIHYDRATE

CROSS REFERENCE TO RELATED APPLICATIONS

This application is the U.S. National Stage of International Application No. PCT/EP2008/004755, filed Jun. 12, 2008, which claims the benefit of German Patent Application No. 10 2007 027 067.6, filed Jun. 12, 2007, each of which is hereby incorporated by reference.

The present invention relates to a process for the preparation of a medicament containing vardenafil hydrochloride trihydrate in solid form, in which vardenafil hydrochloride trihydrate is processed with suitable pharmaceutical auxiliaries at a temperature of from approx. 20° C. to approx. 45° C.

Vardenafil (IUPAC name: {2-ethoxy-5-[(4-ethyl-1-piperazinyl)sulfonyl]phenyl}-5-methyl-7-propylimidazo-[5,1-f][1,2,4]triazin-4(3H)one) belongs to the group of PDE-V (phosphodiesteras V) inhibitors and is used in particular as the hydrochloride as the hydrochloride trihydrate for treatment of erectile dysfunction (see e.g. WO2004/006894). The preparation of vardenafil can be carried out, for example, in accordance with M. Lögers ("Vardenafil—Development of an Effective Route for Commercial Manufacture") 24th SCI Process Development Symposium, Churchill College, Cambridge, UK (12.6.-8.06).

Vardenafil formulations or PDE-V inhibitor formulations generally are chiefly described for inhalation (aerosols, aerosol particles, buccal spray, pump spray) and in the form of chewing gum, and less often in tablet form.

In the preparation of tablets containing vardenafil hydrochloride trihydrate, it is generally a problem that the trihydrate is not stable in one of the processing steps or during coating of the tablets. A loss of hydrate occurs, as a result of which the active compound is not present in the tablets in a uniform form. It is therefore necessary e.g. to treat the tablets with moisture from the atmosphere for several hours after film coating. The trihydrate reforms again by uptake of moisture. This operation can take several hours, depending on the atmospheric humidity, and therefore leads to an adverse delay in the process (see WO2004/006894).

However, it is also known that the water content of an active compound can influence its release from the formulation, which is also a disadvantage. In general, solvent-free medical preparations have considerably higher rates of solution than the corresponding hydrates. In this respect, variations in the water content are to be avoided.

Furthermore, mechanical processes, such as e.g. grinding and pressing, can also have an effect on the reactivity of the active compound to water vapor and to moisture content.

Interestingly, these problems are not referred to in the literature (see e.g. WO2006/092222, WO2006/092207, WO2005/110419 or WO2005/110420).

The object of the present invention was therefore to provide a process for the preparation of tablets with vardenafil hydrochloride trihydrate, in which a loss of hydrate (over-drying) is substantially avoided from the beginning and the additional rehydration step necessary according to WO2004/006894 can be omitted.

It has now been found, surprisingly, that under certain conditions vardenafil hydrochloride trihydrate can be processed to tablets without loss of hydrate.

The present invention therefore provides a process for the preparation of a medicament containing vardenafil hydrochloride trihydrate in solid form, in which vardenafil hydrochloride trihydrate is processed with suitable pharmaceutical auxiliaries at a temperature of from approx. 20° C. to approx. 45° C., preferably from approx. 20° C. to approx. 40° C., in particular from approx. 20° C. to approx. 35° C., above all from approx. 20° C. to approx. 30° C. and particularly preferably at approx. 23° C. Accordingly, the processing temperature according to the present invention should not exceed approx. 45° C.

In the context of the present invention, unless stated otherwise the term "temperature" or "processing temperature" is understood as meaning the product temperature, i.e. the temperature of the medicament formulation during the processing.

Under the conditions mentioned, it is advantageous if the relative humidity of the processing atmosphere is approx. 30% to approx. 90%, preferably approx. 30% to approx. 50%, in particular approx. 30% to approx. 40%, above all approx. 33% to approx. 35%.

In particular, the process according to the invention should be at a processing temperature of approx. 23° C. and a processing atmosphere of from approx. 33% to approx. 35% relative humidity.

The preparation of tablets is generally carried out in several steps. In the process according to the invention, the vardenafil hydrochloride trihydrate is mixed with suitable pharmaceutical auxiliaries in a first step, the mixture is then pressed and the tablets are optionally coated with a film. It is particularly preferable here if the processed medicament is coated with a film in the further step at a temperature of from approx. 40° C. to approx. 55° C., preferably at approx. 40° C. to approx. 50° C., in particular at approx. 45° C.

The tolerance limits (approx. ranges) in the process according to the invention are in general +/−2° C.

In particular, the process according to the invention comprises the following steps:
(a) precompacting of the active compound vardenafil hydrochloride trihydrate in the presence of suitable pharmaceutical auxiliaries,
(b) subsequent mixing with further suitable pharmaceutical auxiliaries,
(c) pressing and optionally
(d) coating, i.e. coating with a film.

In a particular embodiment, the process according to the invention comprises no precompacting of the active compound vardenafil hydrochloride trihydrate in the presence of suitable pharmaceutical auxiliaries, i.e. the active compound is merely mixed with suitable pharmaceutical auxiliaries, the mixture is pressed and the tablets are optionally coated with a film.

In the process according to the invention, the pharmaceutical auxiliaries mentioned are preferably chosen from binders, flow regulators and/or lubricants and optionally also from fillers and/or disintegrating agents (dissociating agents) and optionally a film-forming agent.

Step (a) of the process according to the invention (precompacting) is preferably carried out here in the presence of at least one binder. Step (b) of the process (the subsequent mixing) is preferably carried out with at least one flow regulator and at least one lubricant. Step (d) of the process (coating) is preferably carried out with at least one film-forming agent.

The binder used is above all cellulose, in particular microcrystalline cellulose or microfine cellulose, one or more cellulose derivatives, in particular hydroxypropylmethylcellulose or hydroxypropylcellulose, polyvinylpyrrolidone and/or starch. Microcrystalline cellulose is used in particular as the binder.

The flow regulator added is above all silicon dioxide or a glycerol fatty acid ester, e.g. Boeson® VP (BakerMark Deutschland GmbH), a mixture of mono-, di- and triglycerides. Silicon dioxide is used in particular as the flow regulator.

In a preferred embodiment, the flow regulator is colloidal silicon dioxide ($SiO_2$; silica) or Syloid® 244 FP (Grace GmbH, Germany; trade name for a synthetic porous and amorphous silica having a content of 99.7-99.8% $SiO_2$, max. 0.009% iron and max. 0.1% $SO_4$).

The lubricant used is above all magnesium stearate, calcium stearate, fumaric acid, sodium stearyl fumarate, stearic acid, talc, starch and/or solid polyethylene glycols. The lubricant magnesium stearate is used in particular.

The additional disintegrating agent used is above all crosslinked polyvinylpyrrolidone, starch, sodium carboxymethylstarch (synonym: sodium starch glycollate), carboxymethylcellulose (synonym: carmellose), alginic acid, calcium alginate, pectic acid, formaldehyde-gelatins and/or amylose. The disintegrating agent crosslinked polyvinylpyrrolidone (synonym: crospovidone) is used in particular.

In a particular embodiment, the disintegrating agent is crosslinked carboxymethylcellulose (synonym: croscarmellose), crosslinked sodium carboxymethyl-cellulose (synonym: croscarmellose sodium) or maize starch.

The additional filler used is above all microcrystalline cellulose, starch, mono- and disaccharides, above all lactose, glucose and sucrose, sugar alcohols, above all mannitol and sorbitol, dicalcium phosphate and/or calcium carbonate. The filler microcrystalline cellulose is used in particular.

In a particular embodiment, the filler is modified starch (starch 1500).

Film-forming agents which are used are above all water-soluble cellulose derivatives, above all methylcellulose, hydroxypropylmethylcellulose, hydroxypropylcellulose, hydroxyethylcellulose and sodium carboxymethylcellulose, water-insoluble cellulose derivatives, above all ethylcellulose, cellulose acetate phthalate and hydroxypropylmethylcellulose phthalate, polyacrylates, polymethacrylates, polyvinylpyrrolidone, polyvinyl acetate phthalate, polyvinyl acetate, polyvinyl alcohols, polyethylene glycol, fats and sugar syrup. A mixture of hydroxypropylmethylcellulose and polyethylene glycol is used in particular as the film-forming agent. The film can also contain one or more pigments, for example an iron oxide, aluminum oxide and/or titanium dioxide.

In a particular embodiment, the film-forming agent is Opadry II® (Colorcon; F.D. Enterprise Corp./Pharma Dynamics, Inc.) based on HPMC (hydroxypropylmethylcellulose) or based on PVA (polyvinyl alcohol). Opadry II® is the name of a commercially available tablet coating composition which comprises a mixture of lactose, Methocel HPMC copolymer, polyethylene glycol and desired pigments.

Some film-forming agents which can be used at a relatively low temperature (down to 45° C.) are given as examples in the following table.

| Film-forming agent | Suitable temperature during coating and drying |
| --- | --- |
| Cellulose derivatives | 40-45° C. |
| Polyvinyl alcohols | 30-40° C. |
| Polyvinylpyrrolidone | |
| Polyvinyl acetate | |
| Polymethacrylates | 30-35° C. |
| Sugar syrup | 35-40° C. |

The process according to the invention is carried out above all as follows:

(a) precompacting of a mixture of, for example, sieved, crosslinked polyvinylpyrrolidone, e.g. Kollidon®CL (BASF AG), and microcrystalline cellulose, e.g. Avicel® (FMC Corp.), as the binder and the active compound vardenafil hydrochloride trihydrate, (b) comminuting of the compacted mixture from step (a) and subsequent mixing with, for example, sieved, highly disperse, hydrophilic silicon dioxide, e.g. Aerosil® 200 (Degussa AG), as the flow regulator and sieved magnesium stearate as the lubricant, (c) pressing and optionally (d) coating with an aqueous solution of; for example, hypromellose (hydroxypropylmethylcellulose), e.g. Methocel® (The Dow Chemical Company), and polyethylene glycol 400, e.g. Lutrol® E400 (BASF AG), optionally in the presence of iron oxide pigments and titanium dioxide pigments, e.g. Sicovit® yellow (BASF AG) and Sicovit® red (BASF AG).

The room temperature here is preferably approx. 23° C. and the relative humidity 33-35%.

Lacquered tablets as described, for example, in Examples 3 and 6 of WO 2004/006894 can be prepared in accordance with the present invention. The dose of active compound advantageously varies in the range of approx. 1-100 mg, in particular approx. 2-50 mg, for oral use on humans.

The following figures and examples are intended to explain the invention in more detail without limiting it.

FIGURES

FIG. 1: Raman spectra of the samples vardenafil hydrochloride trihydrate, vardenafil hydrochloride, tablets of Examples 1 to 4

Figure 2:
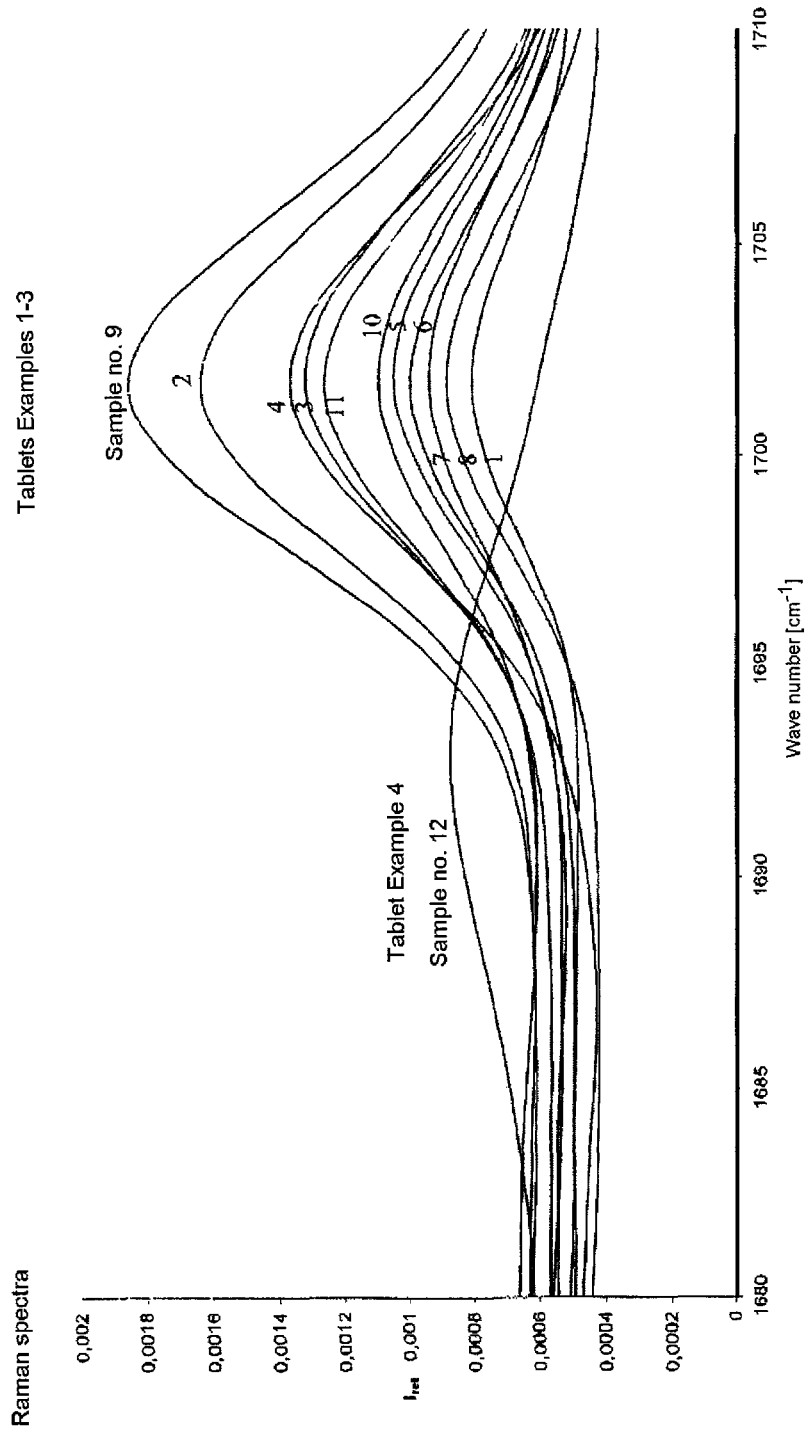

FIG. 2: Raman spectra of the tablets from Examples 1 to 4 (enlarged)

Figure 3:
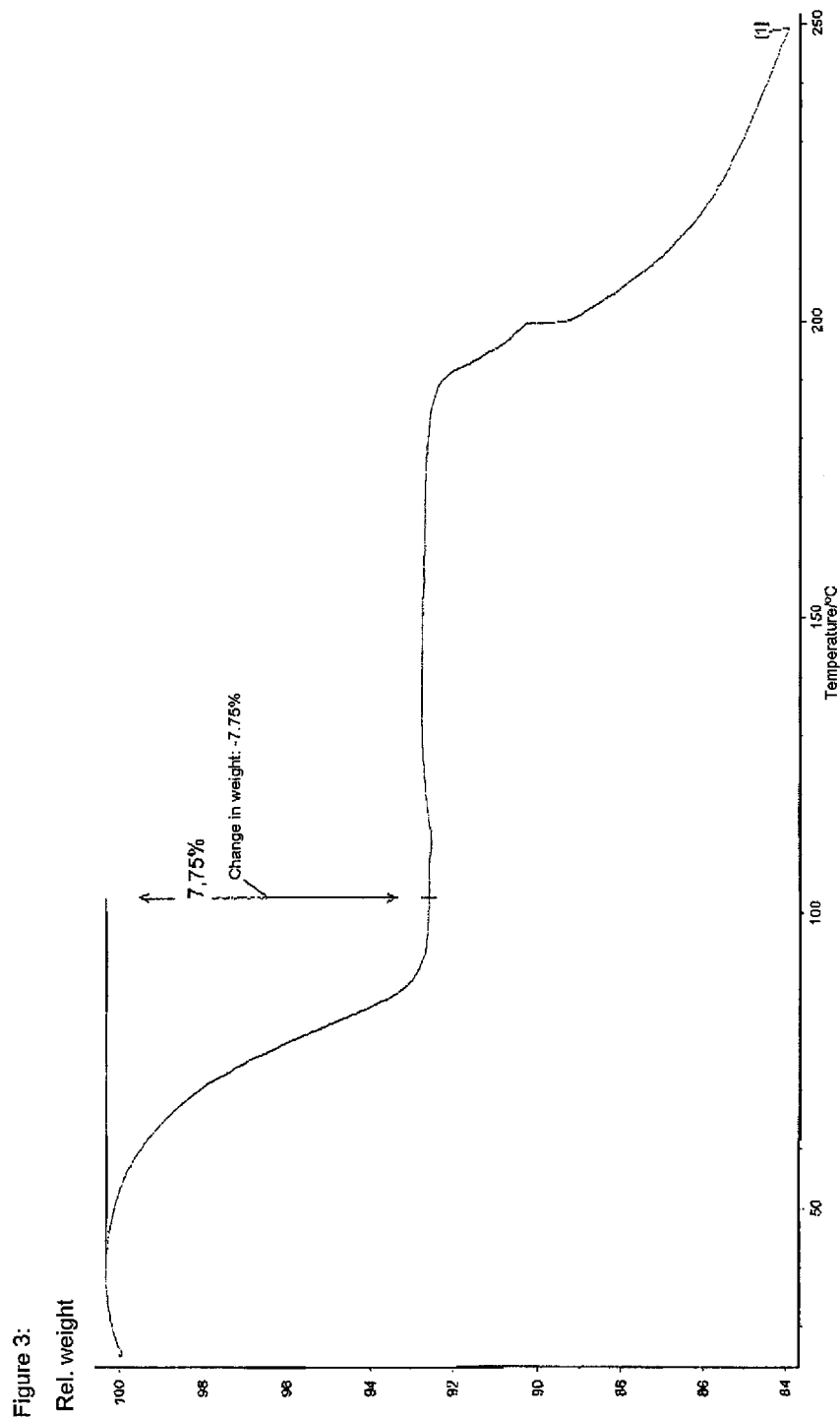

FIG. 3: TGA curve of vardenafil hydrochloride trihydrate

EXAMPLES

Vardenafil hydrochloride trihydrate was prepared in accordance with Example 336 from WO99/24433.

In order to investigate the influence of mechanical forces on the water content of the vardenafil hydrochloride trihydrate, the substance was ground with a CoMill (first over a rasp sieve of 1 mm at 1,500 rpm, then over a sieve of 0.8 mm at 1,500 rpm and finally over a further sieve of 0.5 mm at 2,500 rpm).

The water content of the trihydrate was determined by means of Karl Fischer titration before and after the grinding. The measurement was carried out after heating in a coulometric measuring cell. The results show that the water content does not change significantly due to the grinding and (within the measurement accuracy) is in good agreement with the theoretical value of 9.33 wt. % for the trihydrate. A water content of 9.4% (Karl Fischer) is stated in WO99/24433 (page 263, Example 336). A water content of 9.3% is stated in WO2004/006894 (page 4).

Results of the Karl Fischer Water Content:

Vardenafil hydrochloride trihydrate, non-ground

| | Heating temperature 130° C. |
| --- | --- |
| 1 | 9.39% |
| 2 | 9.36% |

Vardenafil Hydrochloride Trihydrate, Ground:

|   | Heating temperature | | | |
|---|---|---|---|---|
|   | 105° C. | 130° C. | 160° C. | Gradient 60-180° C. |
| 1 | 9.29% | 9.37% | 9.34% | 9.23% |
| 2 | 9.33% | 9.35% | 9.32% | 9.33% |

In the thermogravimetric analysis of the vardenafil hydrochloride trihydrate, a clear weight loss was observed at approx. 50-100° C. This indicates that this is the loss of adsorbed water. A small weight loss occurred at approx. 190° C., which indicates water of crystallization (FIG. 3).

A portion of the substance was dried in vacuo at 60° C. in order to obtain the anhydrate as the reference substance. Raman spectra of the trihydrate and anhydrate were recorded.

Vardenafil hydrochloride trihydrate and anhydrate can be identified and distinguished from one another e.g. by means of Raman spectroscopy. In the Raman spectrum vardenafil hydrochloride trihydrate shows a maximum at approx. 1702 $cm^{-1}$, and vardenafil HCl anhydrate has a maximum at approx. 1694 $cm^{-1}$.

Example 1

Preparation of Tablets

Ground vardenafil hydrochloride trihydrate was used for the preparation of tablets according to Example 6 of WO2004/006894.

17.7 g of Kollidon® CL was first passed over a 250 μm sieve. A first amount of Avicel® (115.9 g) and Kollidon® CL (8.6 g) was mixed together with the active compound (47.7 g) in a Turbula for 10 min. A second amount of Kollidon® CL (9.1 g) and Avicel® (167.7 g) was added and the components were mixed in the Turbula for a further 10 min. The mixture was precompacted with a 20 mm ram with various pressing forces.

The tablets obtained were passed over a 3.2 mm rasp sieve from CoMill and comminuted at 1,000-2,000 rpm. Thereafter, the granules were passed again over a 1.9 mm sieve from CoMill and sieved with the same speed settings. 1.76 g of Aerosil® 200 and 3.54 g of magnesium stearate were passed over a 355 μm sieve and mixed with the granules in the Turbula for 5 min (=final mixture).

Tablets weighing 177 mg and with a diameter of 8 mm were pressed under 4 or 9 kN.

The room temperature was approx. 23° C. in the preparation steps, and the rel. humidity was 33-35%.

Precompacted Samples:

Sample no. 1: compacted with 9 kN

Sample no. 2: compacted with 12 kN

Sample no. 3: compacted with 6 kN

Final Mixture:

Sample no. 4

Tablets:

Sample no. 5: pressed with 4 kN

Sample no. 6: pressed with 9 kN

Sample no. 7: pressed with 4 kN

Sample no. 8: pressed with 4 kN

Example 2

Coating of Tablets

The tablets from Example 1 were coated with an aqueous solution and dried. The temperature and drying time were varied.

Preparation of the Coating Solution 1. 4.5 g of Methocel® E5 LV (hypromellose) were dissolved in 61.4 g of water.
2. 1.5 g of Lutrol® E400 (PEG 400) were dissolved in the remainder of the water (30.7 g) and the pigments Sicovit® yellow (0.25 g), Sicovit® red (0.02 g) and 1.2 g of titanium dioxide were dispersed therein by means of an Ultraturrax for 10 min.
3. Mixture 2 was added to mixture 1.

Coating Process Parameters

The tablets were preheated to 45° C. (product temperature)

Volume flow: 60% (corresponds to about 70 $m^3/h$)

Intake air temp.: 45° C.

Waste air temp.: 38-41° C.

Spraying pressure: 1.8 bar

Sample no. 9: after drying for 5 min

Sample no. 10: after drying for 30 min

Example 3

Coating of Tablets

Coating process parameters as in Example 2. The tablets were not preheated.

Sample no. 11: after drying for 5 min

Example 4

Coating of Tablets

Coating process parameters as in Example 2.

The tablets were preheated to 60° C. for 5 min.

Intake air temp.: 60-65° C.

Waste air temp.: 45-50° C.

Product temp.: 58° C.

Spraying pressure: 1.8 bar

Sample no. 12: after drying for 5 min

Raman spectra were recorded after the processing steps of precompacting, subsequent mixing, pressing and coating (FIGS. 1 and 2). For this, the film was scratched off from the film-coated tablets beforehand. The Raman spectra of the pure vardenafil hydrochloride trihydrate and of the anhydrate are also shown for comparison.

In the relevant range of 1694-1702 $cm^{-1}$, the auxiliaries used in Example 1 had no influence on the vardenafil bands (measurement on a placebo tablet is not also shown).

All the tablets of Examples 1 to 3 showed a maximum at approx. 1702 $cm^{-1}$ in the Raman spectrum, just like vardenafil hydrochloride trihydrate. Vardenafil hydrochloride is therefore stable under the processing conditions used, i.e. it is not dehydrated.

In contrast, the maximum of the tablet from Example 4 was at approx. 1694 $cm^{-1}$, as in the case of vardenafil hydrochloride anhydrate. These tablets were sprayed at a higher intake air temperature than the other tablets. The vardenafil hydrochloride trihydrate dehydrated at an intake air temperature of 60-65° C.

Example 5

Formulation

|  | Content (%) | Function |
|---|---|---|
| Composition | | |
| Vardenafil HCl trihydrate | 9.21 | active compound |
| Anhydrous calcium phosphate (DCP) | 41.94 | filler |
| Lactose monohydrate DCL11 | 38.84 | filler |
| Crosslinked sodium carboxymethylcellulose (croscarmellose sodium) | 4.85 | disintegrating agent |
| Extragranular | | |
| SiO$_2$ | 0.89 | flow regulator |
| Magnesium stearate | 1.36 | lubricant |
| Coating | | |
| Opadry II ® (based on HPMC) | 2.91 | film-forming agent |

1) Vardenafil HCl trihydrate is sieved with crosslinked sodium carboxymethylcellulose (croscarmellose sodium) and equal portions of lactose and dibasic calcium phosphate over a 40 mesh (40 #, 425 μm) sieve (ASTM=American Standard for Material Testing).
2) The mixture from step 1 is sieved with the remaining amount of lactose and dibasic calcium phosphate over a 40 mesh sieve (ASTM).
3) The mixture from step 2 is sieved over a 40 mesh sieve (ASTM) in order to ensure a uniform distribution of the active compound.
4) Silicon dioxide is sieved over a 40 mesh sieve (ASTM) and added to the mixture from step 3.
5) Magnesium stearate is passed through a 40 mesh sieve and mixed with the mixture from step 4.
6) The mixture to which the lubricant had been added was pressed using an 8 mm concave standard production means.
7) Core tablets were coated with a film using Opadry II® (based on HPMC), and the preparation temperature was kept at below 42° C.

Example 6

Formulation

|  | Content (%) | Function |
|---|---|---|
| Composition | | |
| Vardenafil HCl trihydrate | 11.35 | active compound |
| Starlac (85% alpha-lactose monohydrate and 15% maize starch) | 57.15 | filler |
| Maize starch | 20.00 | disintegrating agent |
| Extragranular | | |
| Crospovidone | 5.00 | disintegrating agent |
| SiO$_2$, colloidal | 0.50 | flow regulator |
| Magnesium stearate | 1.50 | lubricant |
| Coating | | |
| Opadry II ® (based on PVA) | 4.00 | film-forming agent |

Example 7

Formulation

|  | Content (%) | Function |
|---|---|---|
| Composition | | |
| Vardenafil HCl trihydrate | 11.85 | active compound |
| Lactose monohydrate (tablettose 80) | 57.15 | filler |
| Maize starch | 20.00 | disintegrating agent |
| Extragranular | | |
| Crospovidone | 5.00 | disintegrating agent |
| SiO$_2$, colloidal | 0.50 | flow regulator |
| Magnesium stearate | 1.50 | lubricant |
| Coating | | |
| Opadry II ® (based on PVA) | 4.00 | film-forming agent |

Example 8

Formulation

|  | Content (%) | Function |
|---|---|---|
| Composition | | |
| Vardenafil HCl trihydrate | 11.85 | active compound |
| Mannitol | 52.15 | filler |
| Hydroxypropylcellulose (HPC LH 11) | 10.00 | binder |
| Maize starch | 15.00 | disintegrating agent |
| Extragranular | | |
| Crospovidone | 5.00 | disintegrating agent |
| SiO$_2$, colloidal | 0.50 | flow regulator |
| Magnesium stearate | 1.50 | lubricant |
| Coating | | |
| Opadry II ® (based on PVA) | 4.00 | film-forming agent |

Example 9

Formulation

|  | Content (%) | Function |
|---|---|---|
| Composition | | |
| Vardenafil HCl trihydrate | 11.85 | active compound |
| Modified starch (starch 1500) | 60.15 | filler |

-continued

| | Content (%) | Function |
|---|---|---|
| Maize starch | 20.00 | disintegrating agent |
| Extragranular | | |
| Crospovidone | 2.00 | disintegrating agent |
| SiO₂, colloidal | 0.50 | flow regulator |
| Magnesium stearate | 1.50 | lubricant |
| Coating | | |
| Opadry II ® (based on PVA) | 4.00 | film-forming agent |

Example 10

Formulation

| | Content (%) | Function |
|---|---|---|
| Composition | | |
| Vardenafil HCl trihydrate | 11.85 | active compound |
| Microcrystalline cellulose | 55.15 | binder |
| Hydroxypropylcellulose (HPC LH 11) | 5.00 | binder |
| Maize starch | 20.00 | disintegrating agent |
| Sodium starch glycollate | 2.00 | disintegrating agent |
| Extragranular | | |
| Syloid ® 244 FP (precipitated silicon dioxide) | 0.50 | flow regulator |
| Sodium stearyl fumarate | 1.50 | lubricant |
| Coating | | |
| Opadry II ® (based on PVA) | 4.00 | film-forming agent |

The invention claimed is:

1. A process for the preparation of a medicament containing vardenafil hydrochloride trihydrate in solid form, characterized in that vardenafil hydrochloride trihydrate is processed with suitable pharmaceutical auxiliaries at a temperature of from approx. 20° C. to approx. 45° C., the relative humidity of the processing atmosphere is approx. 30% to approx. 90%, and the processed medicament is coated with a film in a further step at a temperature of from approx. 40° C. to approx. 55° C., the entire process being carried out without a rehydration step, whereby vardenafil hydrochloride trihydrate is processed to the medicament in solid form without loss of hydrate during the entire process.

2. The process as claimed in claim 1, characterized in that the processing temperature is approx. 23° C. and the processing atmosphere is at approx. 33% to approx. 35% relative humidity.

3. The process as claimed in claim 1, characterized in that the vardenafil hydrochloride trihydrate is mixed with suitable pharmaceutical auxiliaries in a first step, the mixture is then pressed and the tablets are coated with a film.

4. The process as claimed in claim 1, comprising the following steps:
   (a) precompacting of the active compound vardenafil hydrochloride trihydrate in the presence of suitable pharmaceutical auxiliaries,
   (b) subsequent mixing with further suitable pharmaceutical auxiliaries,
   (c) pressing and
   (d) coating.

5. The process as claimed in claim 4, characterized in that according to step (a) the precompacting is carried out in the presence of at least one binder.

6. The process as claimed in claim 4, characterized in that according to step (b) the subsequent mixing is carried out with at least one flow regulator and at least one lubricant.

7. The process as claimed in claim 4, characterized in that according to step (d) the coating is carried out with at least one film-forming agent.

8. The process as claimed in claim 1, characterized in that the suitable pharmaceutical auxiliaries are chosen from binders, flow regulators and/or lubricants and optionally also from fillers and/or disintegrating agents (dissociating agents) and optionally a film-forming agent.

9. The process as claimed in claim 8, characterized in that the binder is chosen from cellulose, cellulose polyvinylpyrrolidone, or starch.

10. The process as claimed in claim 8, characterized in that the flow regulator is chosen from silicon dioxide and/or a glycerol fatty acid ester.

11. The process as claimed in claim 8, characterized in that the lubricant is chosen from magnesium stearate, calcium stearate, fumaric acid, sodium stearyl fumarate, stearic acid, talc, starch, and/or solid polyethylene glycols.

12. The process as claimed in claim 8, characterized in that the disintegrating agent is chosen from crosslinked polyvinylpyrrolidone, starch, sodium carboxymethylstarch, carboxymethylcellulose, alginic acid, calcium alginate, pectic acid, formaldehyde-gelatins, and/or amylose.

13. The process as claimed in claim 8, characterized in that the filler is chosen from microcrystalline cellulose, starch, mono- and disaccharides, sugar alcohols, and/or calcium carbonate.

14. The process as claimed in claim 8, characterized in that the film-forming agent is chosen from water-soluble cellulose derivatives, water-insoluble cellulose derivatives, polyacrylates, polymethacrylates, polyvinylpyrrolidone, polyvinyl acetate phthalate, polyvinyl acetate, polyvinyl alcohols, polyethylene glycol, or fats and sugar syrup.

15. The process as claimed in claim 8, characterized in that the flow regulator is colloidal silicon dioxide or precipitated silicon dioxide, the disintegrating agent is crosslinked carboxymethylcellulose (croscarmellose), crosslinked sodium carboxymethylcellulose (croscarmellose sodium), or maize starch, the filler is modified starch or the film-forming agent is based on HPMC (hydroxypropylmethylcellulose) or based on PVA (polyvinyl alcohol).

16. The process as claimed in claim 3, characterized in that the process comprises no precompacting of the active compound vardenafil hydrochloride trihydrate.

17. The process as claimed in claim 3, characterized in that the film contains one or more pigments.

18. The process as claimed in claim 17, characterized in that the pigment is chosen from iron oxide, aluminum oxide and/or titanium dioxide.

19. The process as claimed in claim 1, wherein said temperature of from approx. 20° C. to approx. 45° C. is approx. 23° C.

20. The process as claimed in claim 1, wherein said relative humidity of the processing atmosphere is approx. 33% to approx. 35%.

21. The process as claimed in claim 1, wherein said temperature of from approx. 40° C. to approx. 55° C. is approx. 45° C.

* * * * *